United States Patent [19]

Liang et al.

[11] Patent Number: 5,504,245
[45] Date of Patent: Apr. 2, 1996

[54] PROCESSES FOR THE PREPARATION OF CYCLOPROPANECARBOXYLIC ACID AND DERIVATIVES THEREOF

[75] Inventors: Shaowo Liang, Kingsport; Timothy W. Price, Church Hill, both of Tenn.

[73] Assignee: Eastman Chemical Company, Kingsport, Tenn.

[21] Appl. No.: 315,462

[22] Filed: Sep. 30, 1994

[51] Int. Cl.$^6$ .............................. C07C 61/04; C07C 62/00
[52] U.S. Cl. ............................................ 562/506; 562/861
[58] Field of Search ................................... 562/506, 861

[56] References Cited

U.S. PATENT DOCUMENTS 4,518,797  5/1985  Roman .................................. 560/231

Primary Examiner—José G. Dees
Assistant Examiner—Rosalynd A. Williams
Attorney, Agent, or Firm—J. Frederick Thomsen; Harry J. Gwinnell

[57] ABSTRACT

Disclosed is a process for the preparation of cyclopropanecarboxylic acid by the non-catalytic, oxidation of cyclopropanecarboxaldehyde using molecular oxygen as the oxidant. Also disclosed are processes for the preparation of amides, esters and acid chlorides from cyclopropanecarboxylic acid.

8 Claims, No Drawings

PROCESSES FOR THE PREPARATION OF CYCLOPROPANECARBOXYLIC ACID AND DERIVATIVES THEREOF

This invention pertains to a process for the preparation of cyclopropanecarboxylic acid by the non-catalytic, oxidation of cyclopropanecarboxaldehyde. This invention also pertains to processes for the preparation of esters and the amide and acid chloride of cyclopropanecarboxylic acid.

Cyclopropanecarboxylic acid and its derivatives, especially cyclopropylamine, are useful in the synthesis of pharmaceuticals and pesticides. See, for example, European Patent Publications EP 237,955 A2, EP 273,862 A2 and EP 430,847 A1. The synthesis of cyclopropanecarboxylic acid by a three-step process consisting of (1) the reaction of a metal cyanide with 1-bromo-3chloropropane to obtain 4-chlorobutyronitrile, the cyclization of the 4-chlorobutyronitrile to obtain cyclopropanenitrile, and (3) the hydrolysis of the cyclopropanenitrile to obtain cyclopropanecarboxylic acid is disclosed in Japanese Patent Kokai 04077453, Org. Synthesis, Coll. Vol. 1, 156 (1941) and Org. Synthesis, Coll. Vol. 3,221 (1955). This process requires handling of an extremely toxic metal cyanide and extensive extractions in the isolation of the product. Additional processes for the synthesis of cyclopropanecarboxylic acid on a laboratory scale are described by J. Tu et al., Youji Huaxue 12, pp. 48–50 (1992); J. Yang et al., Huaxue Shijie 31, pp. 356–358 (1990); M. A. Cohen et al., Tetrahedron Letter 31, 7223–7226 (1990); C. W. Jefford et al., J. Chem. Soc. Chem. Commun., pp. 634–635 (1988); S.C. Bunce et al. Org. Prep. Proced. Int., 6, pp. 193–196 (1974); G. M. Lampan et al., J. Chem. Eng. Data. 14, pp. 396–397 (1969). While convenient for laboratory use, the procedures in these cited articles are not suitable for large-scale commercial use due to low yields and/or the use of expensive reagents.

U.S. Pat. No. 3,711,549 discloses the preparation of methyl cyclopropanecarboxylate by the steps of (1) converting γ-butyrolactone to 4-chlorobutyric acid by cleaving γ-butyrolactone in the presence of zinc chloride at 120° C. and 20.7 bars, (2) reacting the 4-chlorobutyric acid with methanol, and (3) cyclizing the methyl 4-chlorobutyrate. The cyclization reaction requires preesterification of the acid since the cyclization condition otherwise would result in conjugative polymerization of the butyric acid moiety or ring closure to reform gamma-butyrolactone. The process of U.S. Pat. No. 3,711,549 requires handling strongly corrosive and hazardous hydrogen chloride in the gaseous state at elevated temperatures and pressures. The process also involves the use of sodium metal in the manufacture of the fresh sodium methoxide needed for the ring closure of 4-chlorobutyrate ester to yield cyclopropanecarboxylate ester. The mentioned requirements of the process described in U.S. Pat. No. 3,711,549 present serious problems with respect to safety in equipment design and material handling.

U.S. Pat. No. 4,590,292 describes a route to cyclopropanecarboxamide from γ-butyrolactone via a four step process. γ-Butyrolactone is cleaved with hydrogen chloride gas in the presence of aqueous sulfuric acid solution to form 4-chlorobutyric acid which is converted into a chlorobutyrate ester. The chlorobutyrate ester is cyclized by sodium hydroxide in the presence of a phase transfer catalyst to yield a cyclopropanecarboxylate ester. This ester is treated with ammonia in the presence of a sodium alkoxide as a catalyst to form cyclopropanecarboxamide. Like the process of U.S. Pat. No. 3,711,549, this process requires the handling of hydrogen chloride gas at elevated temperatures and pressures. To facilitate ring closure of the 4-chlorobutyrate ester to yield the cyclopropanecarboxylate ester, the use of a secondary or tertiary alcohol in the esterification of 4-chlorobutyric acid is essential. Otherwise hydrolysis of the ester becomes a major competitive reaction leading to low yields (U.S. Pat. No. 3,711,549). It is known that esterification using hindered alcohols presents difficulties in driving the reaction to completion. Long reaction times and continuous removal of water (azeotrope with a organic solvent) are required, which leads to higher costs in manufacturing. The cyclization step of this process requires the handling of a chlorinated solvent such as dichloromethane in order to perform the phase transfer-catalyzed cyclization. In the amidation step of the process of U.S. Pat. No. 4,590,292, typically more than 20 mole percent of sodium alkoxide is needed for effective reaction rates. As a result, the isolation of the product from the reaction mixture is difficult and, based on the examples given, the product usually is obtained as a solution of methanol. In the case of the isolation of a pure product, less than a 46% yield is reported. Recycling and repeating the amidation of the mother liquid is required in order to gain higher yields. Since large amounts of catalyst (sodium ethylene glycoxide) are needed, the preparation of the catalyst constitutes an additional step of the process. It is apparent that the process disclosed in U.S. Pat. No. 4,590,292 poses problems with regard to safety and economics.

U.S. Pat. No. 5,068,428 (equivalent of European Patent Specification EP 365,970) discloses a process for the production of cyclopropanecarboxamide by the amidation of isobutyl cyclopropanecarboxylate in the presence of sodium isobutoxide/isobutanol. The isolation of the product from the reaction mixture is not trivial with a moist, salt-containing product usually being obtained. The process has limitations similar to those described in U.S. Pat. No. 4,590,292.

The present invention pertains to the preparation of cyclopropanecarboxylic acid by the non-catalytic, oxidation of cyclopropanecarboxaldehyde which may be obtained by the thermal isomerization or rearrangement of 2,3-dihydrofuran. For example, U.S. Pat. No. 4,275,238 describes passing 2,3-dihydrofuran through a column at 480° C. to obtain cyclopropanecarboxaldehyde having a purity of 90% purity and containing 6.2–6.7% crotonaldehyde. A similar procedure is described by Wilson, J. Amer. Chem. Soc. 69, 3002 (1947). 2,3-Dihydrofuran may be obtained according to the process described in U.S. Pat. No. 5,254,701 by the isomerization of 2,5-dihydrofuran which in turn can be produced by the isomerization of 3,4-epoxy-1-butene as described in U.S. Pat. Nos. 3,932,468, 3,996,248 and 5,082, 956. U.S. Pat. Nos. 4,897,498 and 4,950,773 describe the preparation of 3,4-epoxy-1-butene by selective monoepoxidation of butadiene.

The process of the present invention comprises the preparation of cyclopropanecarboxylic acid by contacting cyclopropanecarboxaldehyde with molecular oxygen at elevated temperature. We have discovered that the novel oxidation process proceeds at an acceptable rate in the absence of a catalyst and a solvent which reduces operating costs and greatly simplifies both isolation of the carboxylic acid product and the equipment required for the operation of the process. The rate of oxidation of cyclopropanecarboxaldehyde to cyclopropanecarboxylic acid has been found to be dependent primarily upon oxygen mass transfer rather than any catalyst action. Since the oxidation of an aldehyde to a carboxylic acid is a free radical process [see, for example, Riley et al., J. Org. Chem. 52, 287 (1987)], partial or complete decomposition of the cyclopropane ring was a potential problem of the oxidation process. Another advantage provided by the oxidation process is that it causes the decomposition of crotonaldehyde, an inevitable impurity of cyclopropanecarboxaldehyde obtained from 2,3-dihydrofuran. Since the boiling points of cyclopropanecarboxylic acid and crotonic acid are 182°–184° C. and 180°–181° C., respectively, the conversion of the crotonaldehyde impurity to crotonic acid during the oxidation of cyclopropanecarboxaldehyde to cyclopropanecarboxylic acid would present a very difficult purification problem.

The elevated temperatures which may be employed in the operation of the present oxidation process are in the range of about 10° to 200° C. although temperatures in the range of about 50° to 100° C. are preferred. Process pressures of about 0.5 to 50 bar absolute may be used with pressures of about 1 to 10 bar absolute being preferred.

The molecular oxygen used in the process of our invention may be provided as substantially pure oxygen, air, oxygen-enriched air or oxygen diluted with one or more inert gases. Normally, the source of the molecular oxygen is air. In the operation of the process air or other oxygen-containing gas is fed with sufficient agitation to the liquid cyclopropanecarboxaldehyde at a rate which results in complete, or substantially complete, conversion of the cyclopropanecarboxaldehyde in from about 2 to 12 hours. Agitation may be provided by mechanical stirrers or by sparging air into a columnar oxidation vessel. The second step of the process of this invention may be carried out in a batch, semi-continuous or continuous mode of operation.

The oxidation process of the present invention is non-catalytic and proceeds at good rates and selectivities in the absence of a catalyst and, therefore, preferably is carried out in the absence of an added oxidation catalyst. However, it is possible to employ a catalyst in the process. Examples of such catalysts include transition metals and compounds thereof such as cobalt acetate, chromium acetate, platinum and chromium acetate hydroxide and alkali metal carboxylate salts such as sodium acetate and sodium cyclopropanecarboxylate. Although not essential to the successful operation of the process, an inert, organic solvent also may be utilized. Examples of such solvents include aliphatic and aromatic hydrocarbons such as cyclohexane, heptane, toluene, xylene and mixed xylene isomers; ethers such as tetrahydrofuran; alcohols such as methanol and ethanol; or the oxidation product. A preferred embodiment of our invention comprises a process for the preparation of cyclopropanecarboxylic acid which comprises the steps of (1) contacting a mixture of 99.5 to 70 weight percent cyclopropanecarboxaldehyde and 0.5 to 30 weight percent crotonaldehyde with molecular oxygen at a temperature of about 50° to 100° C. and a pressure of about 1 to 10 bar absolute; and (2) recovering cyclopropanecarboxylic acid free of crotonic acid.

As mentioned hereinabove, crotonaldehyde is an inevitable impurity of cyclopropanecarboxaldehyde obtained from 2,3-dihydrofuran. The oxidation process of this invention causes decomposition of crotonaldehyde and/or crotonic acid and thus purification of the cyclopropanecarboxylic acid is greatly simplified. In this embodiment of the invention the cyclopropanecarboxaldehyde/crotonaldehyde mixture more typically comprises 99 to 85 weight percent cyclopropanecarboxaldehyde and 1 to 15 weight percent crotonaldehyde.

The cyclopropanecarboxylic acid obtained from the oxidation process may be converted to various derivatives such as esters, acid chlorides and amides. Cyclopropanecarboxylate esters, e.g., compounds having the structure

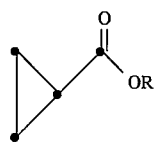

wherein R is defined below, are prepared by reacting cyclopropanecarboxylic acid with various hydroxy compounds at a temperature of about 20° to 200° C., preferably about 60° to 150° C., in the presence of an acidic esterification catalyst. Examples of typical hydroxy compounds include aliphatic, cycloaliphatic and non-aromatic heterocyclic alcohols containing up to about 30, preferably up to about 12, carbon atoms; aromatic, carbocyclic and heterocyclic hydroxy compounds containing 4 to 14 ring carbon atoms such as phenols, napthols and the like. Examples of the hydroxy compound reactants include compounds having the structural formula R-OH wherein R is (i) a linear or branched alkyl, alkenyl or alkynyl radical containing up to about 30 carbon atoms, (ii) a cycloalkyl or cycloalkenyl radical containing 3 to 7 carbon atoms, (iii) a carbocyclic aromatic or heterocyclic aromatic radical which may carry one or more substituents, or (iv) a 5- or 6-membered non-aromatic heterocyclic radical comprising one or more hetero atoms. Exemplary compounds contemplated for use in the practice of the present invention include methanol, ethanol, propanol, isopropanol, butanol, 2-butanol, isobutanol, t-butanol, phenol and benzyl alcohol. Primary and secondary alkanols containing up to about 8 carbon atoms constitute the preferred hydroxy compound reactants.

The alcohol is generally employed in a quantity of 1 to 200 equivalents per equivalent of cyclopropanecarboxylic acid to be converted, preferably 5 to 20 equivalents. Acids which can be used as catalyst for this transformation are: (1) inorganic acids such as sulfuric acid, hydrochloric acid and phosphoric acid; (2) organic acids such as trifluoroacetic acid, p-toluenesulfonic acid, methylsulfonic acid and cyclopropanecarboxylic acid itself. Particularly useful for this reaction is the use of insoluble, acidic, ion exchange resins such as sulfonated polystyrene resins, e.g., Amberlyst XN-1010 and Amberlyst-15 resin beads, and sulfonated polyfluorocarbon resins, e.g., Nafion-H resin. These solid acidic resins are easily separated from the product mixture by filtration and the recovered resins are reusable. The process may be operated batchwise, semi-continuously or continuously. For example, in semi-continuous or continuous operation, cyclopropanecarboxylic acid and an alcohol may be fed to a packed column of the solid acid resin. Recovery and isolation of excess alcohol and the ester product may be accomplished by distillation.

The esterification reaction optionally may be performed in the presence of an organic solvent which forms an azeotrope (constant boiling mixture) with water and thus facilitate the removal of by-product water by azeotropic distillation during the esterification process. Examples of such solvents include aromatic hydrocarbons such as benzene, toluene, xylene and mixed xylene isomers.

Cyclopropanecarbonyl chloride may be prepared by contacting cyclopropanecarboxylic acid with a chlorinating agent at a temperature of about 10° to 120° C. Examples of chlorinating agents include thionyl chloride (see procedure described in J. Chem Soc. Perkin I, pp. 146–147 1976), tetrachloroethylene carbonate (European Patent Specification EP 315,517), phosphorus pentachloride, phosphorus trichloride, oxalyl chloride or phosgene. The mole ratio of the chlorinating agent to cyclopropanecarboxylic acid normally is at least 1:1 and preferably is about 1.1:1 to 1.2:1. The reaction of cyclopropanecarboxylic acid and the chlorinating agent normally is carried out in the absence of either a solvent or a catalyst. The chlorination preferably utilizes thionyl chloride at a temperature of about 50° to 100° C. Upon completion of the reaction (when liberation of gas has stopped), cyclopropanecarbonyl chloride having a purity of at least 98% may be recovered by distillation in yields in the range of 90 to 96%.

Cyclopropanecarboxamide may be obtained by contacting cyclopropanecarboxylic acid with ammonia at a temperature of about 20° to 400° C., preferably 180° to 260° C. and a pressure in the range of 1 to 345 bar absolute. The pressure employed usually depends on the size of the reactor used and preferably is in the range of about 10 to 100 bar absolute. Satisfactory yields usually are achieved using reaction times of about 1 to 10 hours. The amount of ammonia employed in the reaction is in the range of 1 to 50 moles, preferably 3 to 6 moles, per mole of cyclopropanecarboxylic acid. The reaction batch is worked up by venting the reactor with nitrogen at 100° to 150° C. to remove the water along with the excess ammonia. After cooling to room temperature, the product is obtained as a solid which is washed with heptane and collected by filtration to give 99% pure cyclopropanecarboxamide. Such a procedure typically gives an isolated yield of cyclopropanecarboxamide of about 90% at more than 96% conversion of cyclopropanecarboxylic acid.

The reaction of cyclopropanecarboxylic acid with ammonia preferably is carried out in the absence of solvent and catalyst. The exclusion of catalyst and solvents not only provides cost advantages but also simplifies the isolation of the product to give pure cyclopropanecarboxamide suitable for uses in pharmaceuticals and agrochemicals. However, the amidation reaction optionally may be carried out in the presence of an inert, organic solvent. Examples of such solvents include aliphatic and aromatic hydrocarbons such as cyclohexane, heptane, toluene, xylene and mixed xylene isomers, ethers such as tetrahydrofuran, alcohols such as methanol and ethanol.

A particularly useful procedure for the preparation cyclopropanecarboxamide comprises the steps of:

(1) contacting cyclopropanecarboxylic acid with ammonia in a reactor at a temperature of 200° to 260° C., preferably 230° to 240° C., and a pressure of 10 to 100 bar absolute in the absence of both a catalyst and a solvent to form a melt of cyclopropanecarboxamide;

(2) venting the reactor at a temperature above the melting point (120°–122° C.) of cyclopropanecarboxamide, preferably at 130° to 150° C., to reduce the pressure to about atmospheric pressure and remove excess ammonia and water of reaction from the cyclopropanecarboxamide; and (3) obtaining from the reactor cyclopropanecarboxamide essentially free, e.g., containing less than 0.5 weight percent of each, of water and ammonia.

This procedure simplifies the purification of cyclopropanecarboxamide and avoids a potential loss in yield due to the presence of water in which the cyclopropanecarboxamide is soluble.

The processes provided by the present invention are further illustrated by the following examples. Gas chromatographic (GC) analyses were performed on a Hewlett-Packard 5890 series II gas chromatography with a 30 meter DB-Wax and a 30 meter DB-17 capillary columns. The identities of the products obtained were confirmed by nuclear magnetic spectrometry and gas chromatography-mass spectrometry comparing to authentic samples purchased from Aldrich Chemical Company.

EXAMPLE 1

Cyclopropanecarboxaldehyde (105 g, 95% purity, containing 4–4.5% crotonaldehyde) is placed in a steam-jacketed vessel equipped with a mechanical stirrer and a gas inlet at the base of the vessel which then is heated with steam (95°–100° C.). Air is introduced at a rate of 400 mL/minute with agitation for a period of about 8 hours after which time consumption of the cyclopropanecarboxaldehyde is complete as shown by gas chromatography. Distillation of the crude product under reduced pressure gives cyclopropanecarboxylic acid (113 g, 98% purity) in 90% yield.

EXAMPLE 2–7

The procedure described in Example 1 is repeated using 45 g of cyclopropanecarboxaldehyde (except Example 4 in which 56 g of cyclopropanecarboxaldehyde is used) and varying air flow rates and reaction temperatures. The materials listed below are used in Examples 4, 6 and 7:

Example 4—2.16 g of sodium cyclopropanecarboxylate

Example 6—0.5 g of platinum on carbon

Example 7—22.5 mg cobaltous acetate and 22.5 mg of chromium (III) acetate hydroxide The results obtained are shown in Table I wherein Flow Rate is the rate in mL per minute at which air is fed to the gas saturator; Reaction Temperature is the temperature in °C. at which the slightly exothermic oxidation is carried out; and Completion Time is the period of time in hours required to consume all of the cyclopropanecarboxaldehyde. The purity of the cyclopropanecarboxaldehyde obtained was 98% or greater.

TABLE I

| Example | Flow Rate | Reaction Temperature | Completion Time | Isolated Yield, % |
| --- | --- | --- | --- | --- |
| 2 | 400 | 25 | 8 | 85 |
| 3 | 400 | 95–100 | 5 | 88 |
| 4 | 200 | 95–100 | 8 | 85 |
| 5 | 200 | 25 | 12 | 75 |
| 6 | 200 | 25 | 12 | 68 |
| 7 | 200 | 25 | 10 | 92 |

EXAMPLE 8

To a 10-mL, three-necked flask equipped with a condenser, a magnetic stir bar and a thermometer is charged cyclopropanecarboxylic acid (1 g), methanol (5 mL) and 1 drop of concentrated sulfuric acid. The mixture is refluxed (approximately 70° C.) for 3 hours. GC analysis shows complete consumption of the cyclopropanecarboxylic acid and that a quantitative yield of methyl cyclopropanecarboxylate is obtained.

EXAMPLE 9

To a 10-mL, three-necked flask equipped with a condenser, a magnetic stir bar and a thermometer is charged cyclopropanecarboxylic acid (8.6 g), ethanol (23 mL) and 2 drops of concentrated sulfuric acid. The mixture is refluxed (approximately 85° C.) for 16 hours. GC analysis shows that 98% of the cyclopropanecarboxylic acid has been consumed and a 98% yield of ethyl cyclopropanecarboxylate is obtained.

EXAMPLE 10–13

In these examples Amberlyst-15 and Nafion-H acidic ion exchange resins are evaluated as catalysts for the esterification of cyclopropanecarboxylic acid with methanol and ethanol to produce methyl and ethyl cyclopropanecarboxylate. In each example, 2 g of the ion exchange resin, 20 g of cyclopropanecarboxylic acid, and 100 mL of either methanol or ethanol are heated at reflux for a reaction time of up to 20 hours. The consumption of the cyclopropanecarboxylic acid is monitored every 2 hours by GC analysis. In addition to cyclopropanecarboxylic acid, the materials used in each of Examples 10–13 are:

Example 10—Amberlyst-15 resin and methanol
Example 11—Nafion-H resin and methanol
Example 12—Amberlyst-15 resin and ethanol
Example 13—Nafion-H resin and ethanol The results obtained are shown in Table II wherein Total Reaction Time is the hours of reaction time at which the reaction mixture is sampled for GC analysis and the Percent Completion is the mole percent of cyclopropanecarboxylic acid consumed at the time of each analysis.

TABLE II

| Total Reaction Time | Percent Completion | | | |
|---|---|---|---|---|
| | Example 10 | Example 11 | Example 12 | Example 13 |
| 2  | 50.85 | 76.70 | 28.57 | 39.09 |
| 4  | 68.66 | 83.38 | 42.48 | 58.30 |
| 6  | 71.21 | 88.27 | 51.95 | 67.70 |
| 8  | 85.09 | 93.18 | 67.18 | 75.73 |
| 10 | 87.54 | 96.07 | 66.78 | 80.07 |
| 12 | 90.30 | 96.21 | 71.46 | 83.84 |
| 14 | 92.78 | 96.78 | 76.11 | 86.02 |
| 16 | 94.00 | 96.94 | 79.10 | 89.12 |
| 18 | 94.28 | —     | 81.33 | —     |
| 20 | 95.61 | 97.88 | 81.80 | —     |

EXAMPLE 14

To a 50 mL flask equipped with a condenser and an addition funnel is placed cyclopropanecarboxylic acid (8.6 g, 95% assay). To this is added thionyl chloride (13.1 g) dropwise through the addition funnel while stirring. After completion of the addition, the reaction mixture is heated at 80° C. for 30 minutes after which period of time liberation of gas stopped. The mixture is fractionated under reduced pressure to give cyclopropanecarbonyl chloride as a colorless oil (9.4 g, 90% yield, 98% purity by GC).

EXAMPLE 15

To a 500 ml flask equipped with a condenser and an addition funnel, is placed cyclopropanecarboxylic acid (131.6 g, 95% assay). To this is added thionyl chloride (218.9 g) dropwise through the addition funnel while stirring. After completion of the addition over a period of 1.5 hours, the reaction mixture is heated at 80° C. for 30 minutes (liberation of gas stopped). The mixture is fractionated under reduced pressure to give cyclopropanecarbonyl chloride as a colorless oil (164.2 g, 96% yield, 98% purity by GC).

EXAMPLE 16

A 300-mL autoclave is charged with cyclopropanecarboxylic acid (86 g, 95% assay) and ammonia (100 ml), sealed and heated to 240° C. The contents of the autoclave are maintained at 240° C. and 42 to 45 bar absolute for 2 hours. The reaction mixture is cooled to 150° C., the autoclave is vented and nitrogen is circulated through the autoclave at atmospheric pressure. The reaction mixture is allowed to cool to room temperature and the cyclopropanecarboxamide product is collected as solids. GC analysis indicated 96% consumption of the cyclopropanecarboxylic acid. The product is washed with heptane and suction filtered to give 73 g of cyclopropanecarboxamide having a purity of 99% (m.p. 120°–122° C.) in a 90% isolated yield.

EXAMPLE 17

A 300-mL autoclave is charged with cyclopropanecarboxylic acid (129 g, 98% assay) and ammonia (100 ml), sealed and heated to 240° C. The contents of the autoclave are heated with stirring at 240° C. and 41–44 bar absolute for 2 hours. The reaction mixture is cooled to 150° C., the autoclave is vented and nitrogen is circulated through the autoclave at atmospheric pressure. The reaction mixture is allowed to cool to room temperature and the cyclopropanecarboxamide product (119 g, 95% yield, 93% purity by GC) is collected as a solid. GC analysis indicated 94% consumption of the cyclopropanecarboxylic acid. The product is washed with heptane and suction filtered to give cyclopropanecarboxamide having a purity of 99%.

The invention has been described in detail with particular reference to preferred embodiments thereof, but it will be understood that variations and modifications can be effected within the spirit and scope of the invention.

We claim:

1. Process for the preparation of cyclopropanecarboxylic acid which comprises contacting cyclopropanecarboxaldehyde with molecular oxygen at a temperature of about 10° to 200° C.

2. Process according to claim 1 wherein the process is carried out at a temperature of about 50° to 100° C. and the molecular oxygen is provided as substantially pure oxygen, air, or oxygen-enriched air.

3. Process according to claim 1 wherein the process is carried out at a temperature of about 50° to 100° C. and a pressure of about 1 to 10 bar absolute in the presence of an inert, organic solvent and the molecular oxygen is provided as substantially pure oxygen, air, or oxygen-enriched air.

4. Process for the preparation of cyclopropanecarboxylic acid which comprises contacting cyclopropanecarboxaldehyde with molecular oxygen provided as substantially pure oxygen, air, or oxygen-enriched air at a temperature of about 50° to 100° C. and a pressure of about 1 to 10 bar absolute in the absence of an oxidation catalyst.

5. Process for the preparation of cyclopropanecarboxylic acid which comprises the steps of:

(1) contacting a mixture of 99.5 to 70 weight percent cyclopropanecarboxaldehyde and 0.5 to 30 weight percent crotonaldehyde with molecular oxygen at temperature of about 50° to 100° C. and a pressure of about 1 to 10 bar absolute; and (2) recovering cyclopropanecarboxylic acid free of crotonic acid.

6. Process according to claim 5 for the preparation of cyclopropanecarboxylic acid which comprises the steps of:

(1) contacting a mixture of 99 to 85 weight percent cyclopropanecarboxaldehyde and 1 to 15 weight percent crotonaldehyde with molecular oxygen provided as substantially pure oxygen, air, or oxygen-enriched air at a temperature of about 50° to 100° C. and a pressure of about 1 to 10 bar absolute; and (2) recovering cyclopropanecarboxylic acid free of crotonic acid.

7. Process of claim 1 wherein in a second step the cyclopropanecarboxylic acid is reacted with a chlorinating agent selected from thionyl chloride, tetrachloroethylene carbonate, phosphorus pentachloride, phosphorus trichloride and phosgene at a temperature of 10° to 120° C. to produce cyclopropanecarbonyl chloride.

8. Process according to claim 4 wherein in a second step the cyclopropanecarboxylic acid is reacted with thionyl chloride at a temperature of 50° to 100° C. to produce cyclopropanecarbonyl chloride.

* * * * *